(12) United States Patent
Blank

(10) Patent No.: US 6,386,873 B1
(45) Date of Patent: May 14, 2002

(54) DENTAL TOOL

(76) Inventor: Jeff T. Blank, 360 Bailey Ave., Rock Hill, SC (US) 29732

( * ) Notice: Subject to any disclaimer, the term of this patent is extended or adjusted under 35 U.S.C. 154(b) by 0 days.

(21) Appl. No.: 09/740,765

(22) Filed: Dec. 19, 2000

(51) Int. Cl.$^7$ .............................................. A61C 3/02
(52) U.S. Cl. ...................................................... 433/142
(58) Field of Search ................................ 433/141, 142, 433/143, 144, 125, 146

(56) References Cited

U.S. PATENT DOCUMENTS

| | | | |
|---|---|---|---|
| 491,464 A | 2/1893 | Blake, Sr. | |
| 614,723 A | * 11/1898 | Jackson | 433/142 |
| 815,153 A | 3/1906 | Fritz | |
| 1,050,469 A | * 1/1913 | Keifer | 433/142 |
| 1,201,875 A | * 10/1916 | Russ | 433/142 |
| 1,707,952 A | 4/1929 | Schneider | |
| 2,029,495 A | 2/1936 | Lowe | 128/305 |
| 2,655,726 A | 10/1953 | Diener | 32/46 |
| 3,325,900 A | 6/1967 | Sohlberg | 32/46 |
| 4,319,876 A | 3/1982 | Muraoka | 433/141 |
| D265,004 S | 6/1982 | Davis | D28/64 |
| 4,365,957 A | 12/1982 | Das | 433/144 |
| 4,592,729 A | * 6/1986 | Bilciurescu | 433/142 |
| 4,820,154 A | 4/1989 | Römhild et al. | 433/128 |
| 4,836,781 A | 6/1989 | Meinershagen | 433/141 |
| 4,854,867 A | 8/1989 | Meinershagen | 433/40 |
| 4,952,213 A | 8/1990 | Bowman et al. | 606/79 |
| D311,595 S | 10/1990 | Ewald | D28/64 |
| 5,084,978 A | 2/1992 | McReynolds | 30/517 |
| 5,118,291 A | 6/1992 | Varaine | 433/142 |
| 5,682,665 A | 11/1997 | Svanberg | 29/458 |

* cited by examiner

Primary Examiner—Nicholas D. Lucchesi
(74) Attorney, Agent, or Firm—Moore & Van Allen PLLC; Michael G. Johnston

(57) ABSTRACT

A dental tool is provided for use in removing solidified material from on and between teeth during restorations. The new dental tool is appropriately shaped to provide proper control and visualization of the work and prevent damage to the interior of the mouth. The dental tool comprises a handle portion and a blade support portion extending from the handle portion, wherein the longitudinal axis of the handle and blade support portions form an angle of from about 130 degrees to about 140 degrees. A blade member is supported on the distal end of the blade support portion including a support surface which is in a plane which forms an angle of from about 80 degrees to about 100 degrees with the longitudinal axis of the handle portion. The blade supporting portion comprises a pair of spaced arms projecting from the handle and at an angle relative to one another in the range of from about 10 to about 25 degrees. The distal end portion of the spaced arms terminate in bosses, preferably barbs for supporting the blade member. The blade member has mounting holes on each end for receiving the bosses on the ends of the arms. The blade member is fixed to the ends of the arms by compressing the arms inwardly to accommodate the mounting holes in the blade member. Thus, the blade member is quickly and easily replaceable.

20 Claims, 2 Drawing Sheets

DENTAL TOOL

BACKGROUND

The present invention relates to a dental tool, and more particularly to a dental tool for use in the removal of excess solidified composite material from on and between teeth during the cementation of composite and porcelain restorations.

Modern adhesive dentistry has evolved to the point where a majority of dentists are utilizing composite materials to restore human teeth. The use of these and similar materials is expected to increase.

There are essentially two types of restorations that may require the cleaning of excess composite material from between the teeth. The first is an "indirect" restoration, in which a crown, inlay or onlay is fabricated and cemented into place with a cement. Since modern cosmetic materials are made of porcelain or composite, with no metal understructure, strong cements, generally referred to as "luting resins", have been formulated to add strength to prohibit fracture. Luting resins set instantly with exposure to a special curing light. Composites are "direct" restoration materials that are basically tooth colored fillings applied directly to the teeth. Because decay often extends between the teeth, the dentist must shape the composite to seal this area.

During the restoration process, it is quite common for excess composite material to be expressed beyond the margins of the restoration and harden on and between the teeth and under the gum line. Leaving such material can be hazardous to the dental tissues, causing severe irritation, gum disease, and recurrent decay.

Devices have been designed to remove excess solidified composite material from between the teeth. Most of these devices hold a variety of cutting blades and sanding strips of various grits and widths which are worked between and against the teeth to remove the excess material. Considerable manual dexterity and operational skill is required to perform the sawing and abrasive functions within the limited confines of a human mouth. Even assuming the requisite skill, conventional tools are poorly designed for use in all areas of the mouth, especially the posterior teeth. The operation of present day tools is extremely difficult to control and, unless extreme care is taken, an error can result in injury or damage to the fleshy part of the patient's mouth. Moreover, the shape of the tools significantly hinders the visualization of the working areas.

For the foregoing reasons, there is a need for an improved dental tool for use in the removal of excess composite material on or between the teeth during restorations. The tool should provide easy access to all areas of the mouth, including the posterior teeth, while providing ease of control of the oscillatory motions and vertical pressure between the teeth to remove material without danger of slipping or damaging the patient's mouth. The tool should also allow proper visualization of the working area.

SUMMARY

Accordingly, it is an object of the present invention to provide a dental tool for the removal of solidified material between the teeth which provides easy access to all areas of the mouth, particularly the posterior teeth, while providing good visibility of the work in process.

Another object of the present invention is to provide a dental tool which may be used in such a manner while substantially reducing the danger of cutting into the fleshly part of the mouth or the gum.

According to the present invention, a dental tool is provided for use in removing solidified material from on and between teeth during restorations. The dental tool comprises a handle portion and a blade support portion extending from the handle portion, wherein the longitudinal axis of the handle and blade support portions form an angle of from about 130 degrees to about 140 degrees. Means for supporting a blade member are provided on the distal end of the blade support portion including a support surface which is in a plane which forms an angle of from about 80 degrees to about 100 degrees with the longitudinal axis of the handle portion. Further in accordance with the present invention, the handle portion comprises a gripping portion including opposed concave side surfaces for accommodating the thumb and middle finger, respectively, and a flat portion on the top surface of the handle portion between the concave side portions for the index finger.

The blade supporting means comprises a pair of spaced arms projecting from the handle and at an angle relative to one another in the range of from about 10 to about 25 degrees. The distal end portion of the spaced arms terminate in bosses, preferably barbs for supporting the blade member.

The present invention is also concerned with the blade member, which has mounting holes on each end for receiving the bosses on the ends of the arms. The blade member is fixed to the ends of the arms by compressing the arms inwardly to accommodate the mounting holes in the blade member. The biasing force of the arms provides a tension force to immovably secure the blade member to the tool between the arms. The blade member is quickly and easily replaceable.

The new dental tool of the present invention solves the aforementioned problems with present day tools by providing a tool which is appropriately shaped to provide proper control and visualization of the work and prevent damage to the interior of the mouth. The tool facilitates removal of residual solidified composite material on and between the posterior teeth, as well as the anterior teeth. The new dental tool possesses unique angles that render it more efficacious and ergonomic in use.

DRAWINGS

For more complete understanding of the invention, reference should now be had to the embodiment shown in the accompanying drawings and described below. In the drawings, like reference numerals designate corresponding or similar elements throughout the several views.

DESCRIPTION

Figure 1:
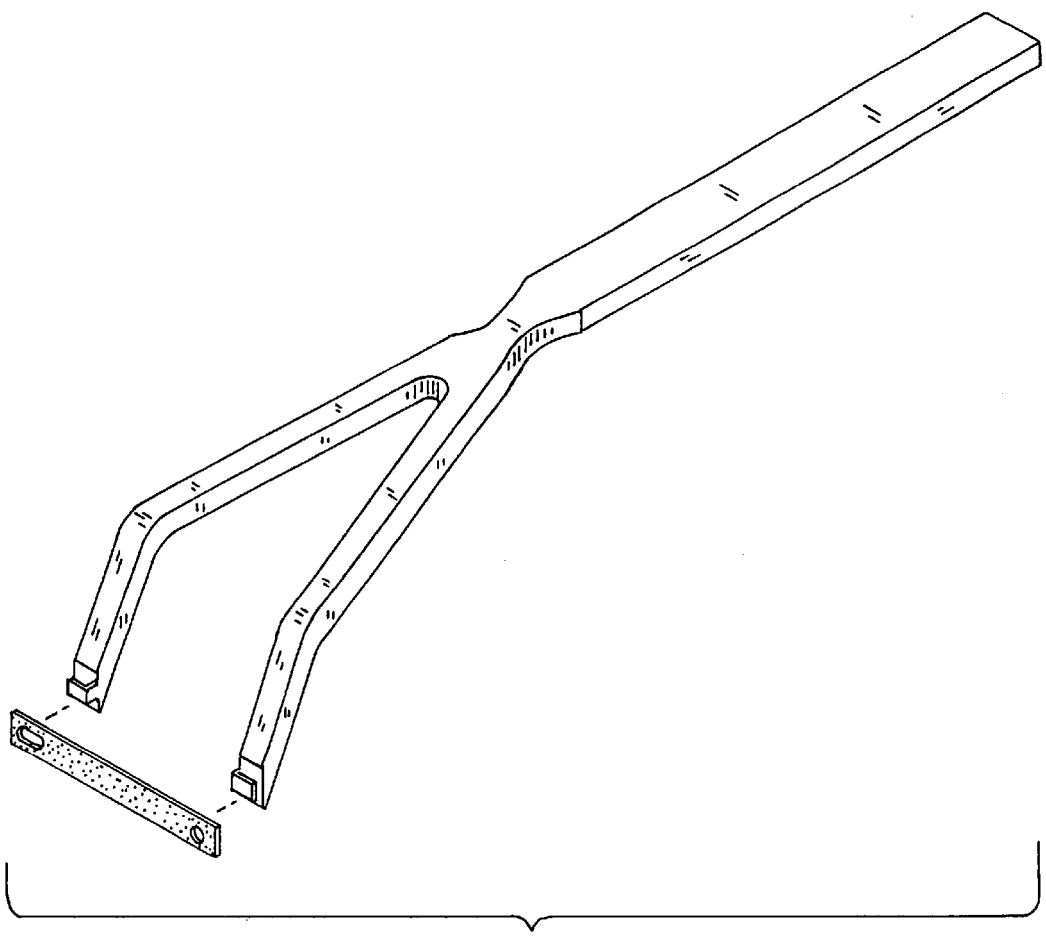
FIG. 1 is an exploded view of a dental tool and blade member according to the present invention.
Figure 2:
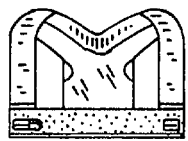
FIG. 2 is a front end view of the dental tool and blade member as shown in FIG. 1 with the blade member in place on the tool.
Figure 3:
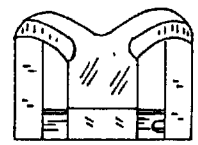
FIG. 3 is a back end view of the dental tool of FIG. 2.

Referring now to the drawings, there is shown a dental tool according to the present invention generally designated at reference numeral 10. The dental tool comprises a handle portion 12, a blade support portion 14 and a blade member 16.

The elongated handle portion 12 extends generally along a major longitudinal axis and terminates at end portions 18, 20. The handle may be of any configuration so as to comfortably fit a user's hand. In the embodiment shown in the FIGs., the handle 12 is a smooth structure having major, flat top 22 and bottom surfaces 24 joined by flat side surfaces 26. Adjacent one end portion 20, the handle 12 has opposed side concavities 28.

The blade support portion 14 comprises first and second arms 30 extending from the end 20 of the handle portion 12 adjacent the concave side portions 28. The blade support portion 14 is preferably integral with the handle portion 12, although the blade support portion may be removably attached to the handle. The distal ends 32 of the arms 30 terminate in working ends having a working surface adapted to support the blade member. The working surfaces 34 include bosses 36 (or protrusions) having a reduced cross-sectional area from that of the arms 30. Preferably, the bosses 36 are shaped like hooks or barbs.

The handle 12 and blade support portions 14 are formed of material which can withstand the chemicals and heat associated with conventional sterilizing techniques, such as solid metal or the like. Particularly useful is chromium steel or stainless steel which will not rust easily during cold sterilization or use in the mouth. The tool may alternatively be made of any other suitable material, including titanium, plastic and nylon, as long as the instrument is autoclavable.

Figure 6:
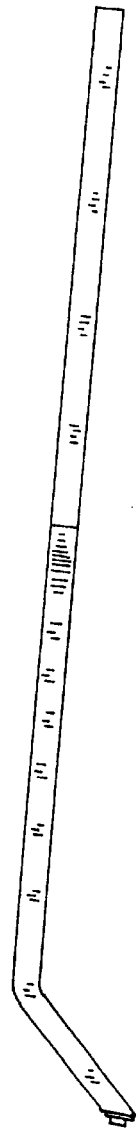
FIG. 6 is a side view of the dental tool of FIG. 2.
Figure 1:
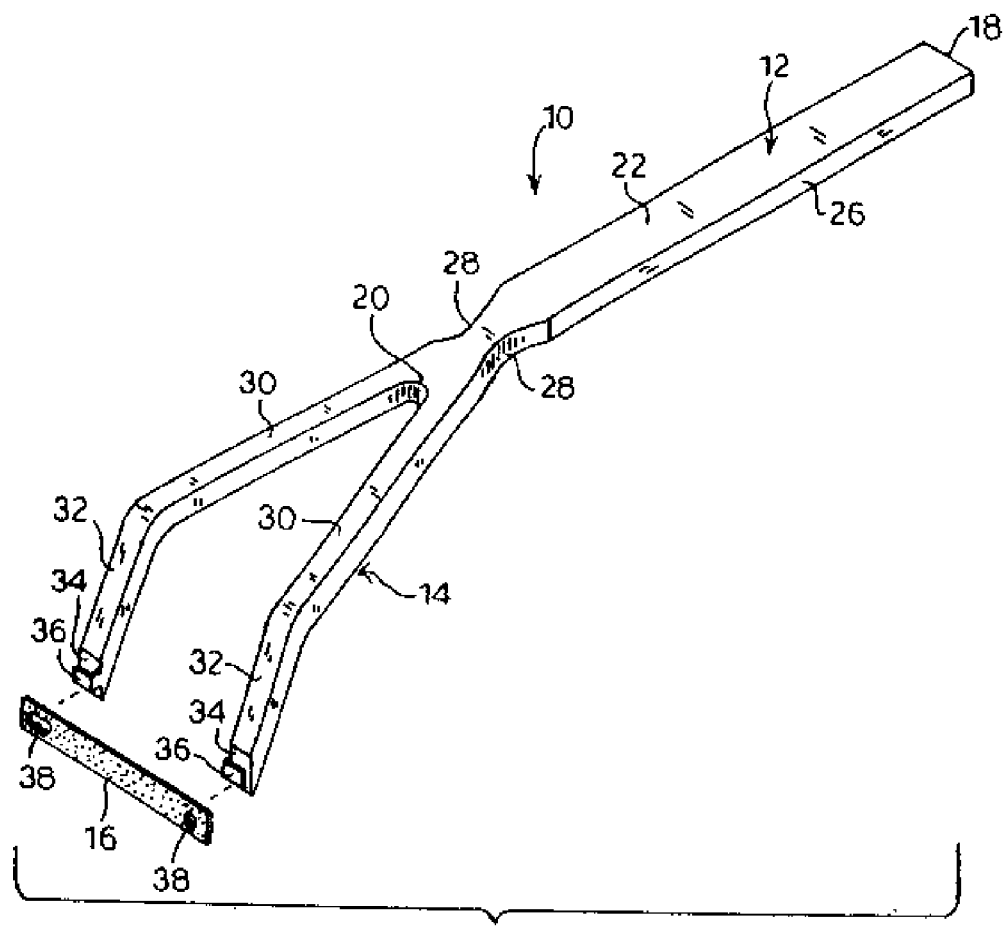
Figure 2:
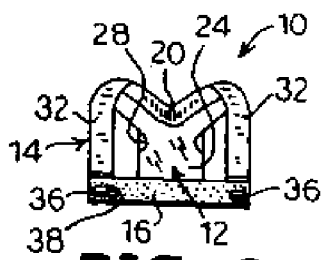
Figure 3:
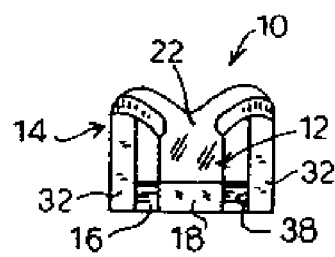
Figure 4:
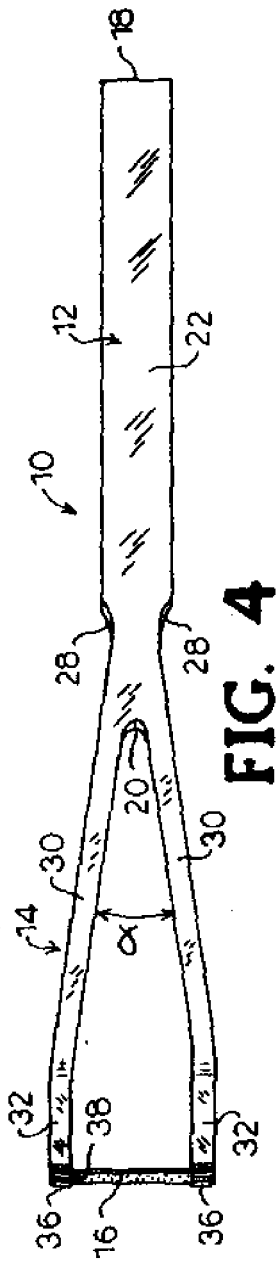
Figure 5:
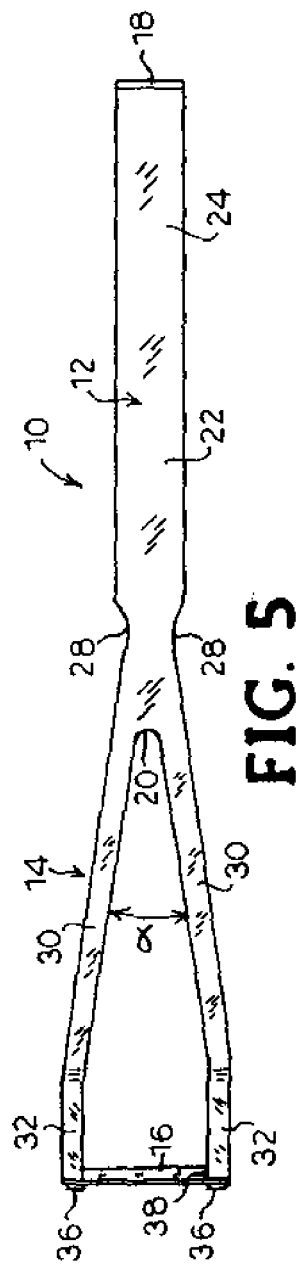
Figure 6:
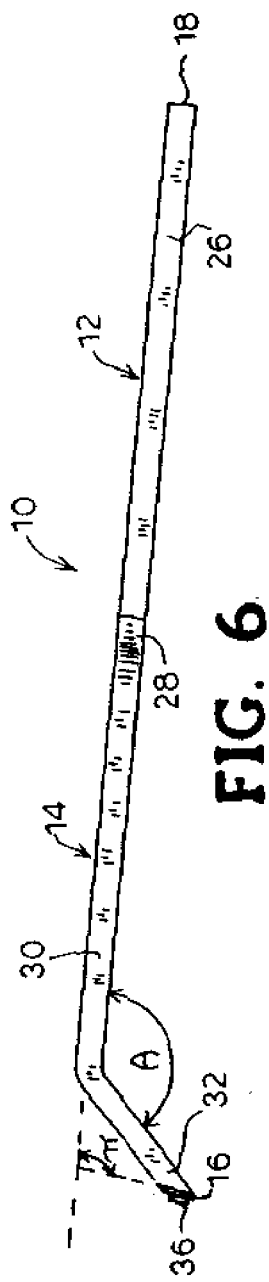

The distal end 32 of each of the arms 30 of the blade support portion 14 is angularly disposed with respect to the longitudinal axis of the handle portion 12. The angle, A (FIG. 6), formed by the longitudinal axis of the handle 12 and the distal ends 32 of the arms 30 of the blade support portion 14 is from about 130 degrees to about 140 degrees, and preferably about 135 degrees. At angles greater than about 140 degrees, obtaining adequate clearance of the handle off of the teeth is difficult, and the handle could damage the biting surfaces of the teeth in the same arch as the operation while the tool is oscillated. At angles less than about 130 degrees, the handle would be elevated off of the biting surfaces of the teeth too much, and push the fulcrum too far away from the teeth. Additionally, there may not be enough freeway space between the upper and lower teeth, especially on posterior teeth distal in the arch, to oscillate the tool without damaging the opposing teeth during the action. It is understood that it may be appropriate in some cases to change the length of the angularly disposed portions 32 of the arms 30 so that less room is required to operate the tool 10 between the upper and lower jaws of the mouth making the tool 10 more suitable for small mouths, such as in pediatric cases.

Figure 4:
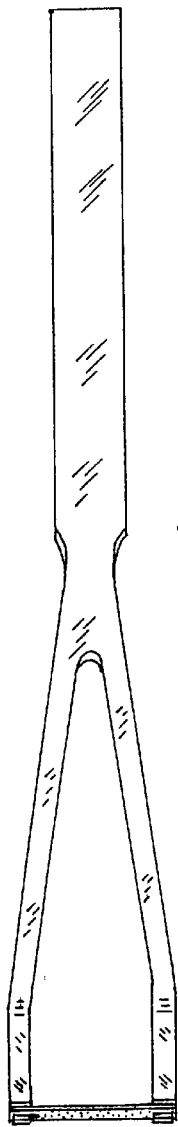
FIG. 4 is a top view of dental tool of FIG. 2.
Figure 5:
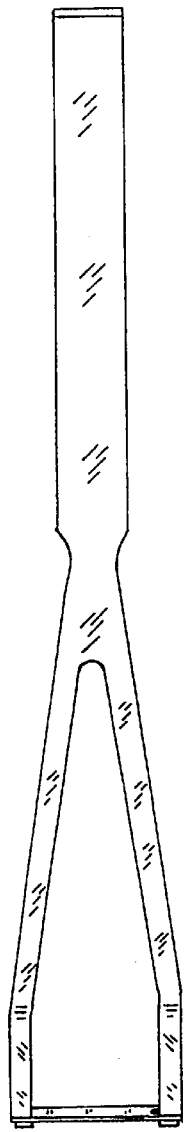
FIG. 5 is a bottom view of the dental tool of FIG. 2.

As best seen in FIGS. 4 and 5, the arms 30 of the blade support portion 14 diverge from one another. Preferably, the angle ($\alpha$) of divergence is from about 10 to about 25 degrees, and more preferably about 15 degrees. This angle of divergence is necessary to permit proper visualization of the working field. If the divergence is less than about 10 degrees, the arms will obstruct the visual field. If the divergence is much more than about 25 degrees, the arms become too wide, and place the cheek tissue (laterally) and the tongue (medially) at risk of laceration. The length of the arms 30 and the angle of divergence are selected so that the distal ends 32 of the arms 30 are at least about one inch apart where the blade member 16 attaches. A one inch blade member 16 is estimated to be the minimal length necessary to effectively remove composite material without injury to the cheek or tongue.

The blade member 16 is generally a thin rectangularly-shaped member with mounting holes 38 on each end. The blade member 16 may have serrated teeth such as a saw blade. The blade member may also be abrasive on one side, or both sides, for abrasive applications of the tool. Abrasive blade members are usually diamond-coated sanding blades which are available in varying widths and grits. Two abrasive sides permit both distal and mesial interproximal surface sanding with a push or pull pressure, respectively. This makes the tool more versatile, allowing the user to work on both the mesial surface of the most distal tooth, and the distal surface of the more mesial tooth, without having to withdraw the tool from between the teeth, change blades, and re-enter the interproximal space. This need is very common when multiple teeth and surfaces are being restored in the same quadrant at the same time.

The blade member 16 is removably mounted on the blade support portion 14 by pressing the arms 30 inwardly towards one another and inserting the bosses 36 through the mounting holes 38 in the blade member 16. When the arms 30 are released, the spring force between the arms provides enough force to hold the blade member 16 securely in place against the working surfaces 34 on the terminal ends of the arms 30. At the same time, the blade members 16 are rapidly changed as necessary. Thus, a user may quickly change from a saw blade to a blade member incorporating polishing or abrasive surfaces. It is understood that if the blade support portion 14 is releasably attached to the handle 12, the blade support portion 14 carrying different type blade members 16 could be interchanged.

The blade member 16 is held against the working surfaces 34 so that the surface of the major faces of the blade member are angularly disposed with respect to the handle portion 12. The angle, $\Pi$ (FIG. 6), formed by the major surfaces of the blade member 16 when in the working position with the longitudinal axis of the handle 12 is from about 80 degrees to about 100 degrees, and preferably about 90 degrees. By properly positioning the faces of the blade member 16 with respect to the handle, the user can work against either the front or back side of a tooth. This orientation also allows the user to easily position the tool 10 in all areas of the mouth to place the blade surface into proper position with respect to the teeth, particularly between posterior teeth. At angles less than about 80 degrees or greater than about 100 degrees, the flat abrasive portion of the blade cannot come into intimate adaptation with the interproximal surface of the tooth during the ergonomic and comfortable oscillation of the handle in a left to right motion along the plane of the major surface of the blade member 16. Additionally, angles less than about 80 degrees or greater than about 100 degrees may permit the edges of the abrasive strip to gouge the tooth and cause damage to soft tissue in the mouth or the tongue.

The user holds the handle 12 of the dental tool 10 firmly in the palm of the hand and places the thumb and middle finger in the concave portions 28 of the handle and the index finger on the flat top surface 22 of the handle 12 between the concave portions. This finger positioning causes the tool 10 to react to controlled hand and finger pressure applied in a direction perpendicular or parallel to the longitudinal axis of the handle. When the blade member 16 is in contact with a tooth, the user forces the cutting edge or abrasive surface of the blade member against the desired portion of the tooth to remove debris. Movement is imparted to the tool by the user for working against the teeth.

The present invention has many advantages, including a dental tool for use in the removal of excess composite material from between the teeth which allows easy manipulation and accessibility to all teeth in the mouth. The preferred angulation of the blade member with respect to the handle portion, and proper finger rests provided on the handle, permits the blade member to be positioned to make appropriate contact with the interproximal surfaces of the posterior teeth. An assortment of cutting blades and sanding strips can be used to not only clear the resin from between the teeth, but sand smooth the surfaces with the various grits. Moreover, the user can exert a great deal of pressure on the blade member while maintaining complete and absolute control of the movement of the cutting or abrasive surface within the very limited space of the mouth. The divergence of the arms of the blade support portion protects the mouth from injury by separating the cheek and the tongue from the cutting or abrasive blade member. Further, the design permits proper visualization of the working area. Thus, removal of solidified resin around the teeth is easily and safely accomplished without the fear of injury brought about by the use of other dental instruments that require significant force or arm movements.

Although the present invention has been shown and described in considerable detail with respect to a particular exemplary embodiment thereof, it should be understood that by those skilled in the art that I do not intend to the limit the invention to the embodiment, its various modifications, omissions and additions may be made to the disclosed embodiment without materially departing from the novel teachings and advantages of the invention particularly in light of the foregoing teachings. For example, it should be understood that any type of handle can be substituted for the handle illustrated, such as a round or more ergonomic handle, and the angles between the handle and blade support portion and blade support member can be varied as required. Accordingly, I intend to cover all such modifications, omissions, and additions and equivalence as may be included within the spirit and scope of the invention as defined by the following claims. In the claims, means plus function clauses are intended to cover the structures described herein as performing the recited function and not only structural equivalence but also equivalent structure. Thus, although a nail and a screw may not be structural equivalence and that a nail includes cylindrical surfaces to secure wood parts together, whereas the screw employs a helical surface, and the environment of fastening wooden parts, a nail and a screw may be equivalent structures.

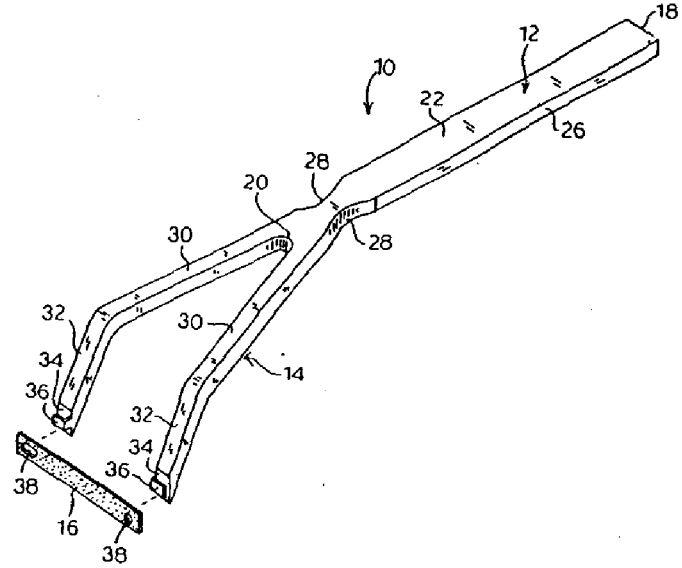

I claim:

1. A dental tool for use in removing solidified material on teeth and between adjacent teeth during restorations, the dental tool comprising:
   a handle portion having a longitudinal axis;
   a blade support portion extending from the handle portion, the blade support portion having a distal end which forms an angle of from about 130 degrees to about 140 degrees and with the longitudinal axis of the handle; and
   means adapted for supporting a blade member on the distal end of the blade support portion, the blade member supporting means including a support surface, wherein the blade member support surface is in a plane which forms an angle of from about 80 degrees to about 100 degrees with the longitudinal axis of the handle portion for better access to the posterior portions of the mouth and control of movement of the tool when in use.

2. A dental tool as recited in claim 1, wherein the handle portion has a gripping portion comprising opposed concave side surfaces for accommodating the thumb and middle finger, respectively, and a flat portion on the top surface of the handle portion between the concave side portions for the index finger.

3. A dental tool as recited in claim 1, wherein the angle formed by the distal end of the blade support portion and the longitudinal axis of the handle is about 135 degrees.

4. A dental tool as recited in claim 1, wherein the angle formed by the plane including the support surface of the blade supporting means and the longitudinal axis of the handle is about 90 degrees.

5. A dental tool as recited in claim 1, wherein the blade supporting means comprises a pair of spaced arms having distal end portions, the arms extending from the handle and at an angle relative to one another wherein the angle formed by the arms is in the range from about 10 degrees to about 25 degrees, and the distal end portions form the blade member support surface.

6. A dental tool as recited in claim 5, wherein the angle formed by the arms is about 25 degrees.

7. A dental tool as recited in claim 5, wherein the length of the arms is selected so that the distance between the distal ends of the arms is at least about one inch.

8. A dental tool as recited in claim 1, further comprising a blade member fixed on the blade supporting means.

9. A dental tool as recited in claim 8, wherein the arms terminate in bosses and the blade member has apertures for receiving the bosses, the blade member affixed to the arms by compressing the arms inwardly to accommodate the mounting holes in the blade, the outward biasing force of the arms forcing the bosses into engagement with the apertures in the blade member and providing the tension force to immovably secure the blade member to the tool between the arms.

10. A dental tool as recited in claim 8, wherein the blade member is a saw.

11. A dental tool as recited in claim 8, wherein the blade member is an abrasive strip.

12. A dental tool as recited in claim 11, wherein the blade member has two oppositely disposed principal abrasive side surfaces and two edge surfaces extending between and interconnecting the side surfaces.

13. A dental tool for use in removing solidified material on teeth and between adjacent teeth during restorations, the dental tool comprising:
   a handle portion having a longitudinal axis;
   a blade support portion extending from the handle portion, the blade support portion having a distal end which forms an angle of from about 130 degrees to about 140 degrees; and with the longitudinal axis of the handle; and
   means adapted for supporting a blade member on the distal end of the blade support portion, the blade member supporting means including a pair of spaced arms having distal end portions, the arms extending from the handle and at an angle relative to one another wherein the angle formed by the arms is in the range from about 10 degrees to about 25 degrees, and a support surface formed on the distal end portions of the arms, wherein the blade member support surface is in a plane which forms an angle of from about 80 degrees to about 100 degrees with the longitudinal axis of the handle portion for better access to the posterior portions of the mouth and control of movement of the tool when in use.

14. A dental tool as recited in claim 13, wherein the angle formed by the distal end of the blade support portion and the longitudinal axis of the handle is about 135 degrees.

15. A dental tool as recited in claim 13, wherein the angle formed by the plane including the support surface of the blade supporting means and the longitudinal axis of the handle is about 90 degrees.

16. A dental tool as recited in claim 13, wherein the angle formed by the arms is about 25 degrees.

17. A dental tool as recited in claim 13, wherein the length of the arms is selected so that the distance between the distal ends of the arms is at least about one inch.

18. A dental tool as recited in claim 13, further comprising a blade member fixed on the blade supporting means.

19. A dental tool as recited in claim 18, wherein the blade member is a saw.

20. A dental tool as recited in claim 18, wherein the blade member is an abrasive strip having two oppositely disposed principal abrasive side surfaces and two edge surfaces extending between and interconnecting the side surfaces.

* * * * *

UNITED STATES PATENT AND TRADEMARK OFFICE
CERTIFICATE OF CORRECTION

PATENT NO. : 6,386,873 B1
DATED : May 14, 2002
INVENTOR(S) : Jeff T. Blank

It is certified that error appears in the above-identified patent and that said Letters Patent is hereby corrected as shown below:

Drawings,
Please replace old drawings with new drawings here

Signed and Sealed this

First Day of March, 2005

JON W. DUDAS
*Director of the United States Patent and Trademark Office*

United States Patent
Blank

(10) Patent No.: US 6,386,873 B1
(45) Date of Patent: May 14, 2002

(54) DENTAL TOOL

(76) Inventor: Jeff T. Blank, 360 Bailey Ave., Rock Hill, SC (US) 29732

(*) Notice: Subject to any disclaimer, the term of this patent is extended or adjusted under 35 U.S.C. 154(b) by 0 days.

(21) Appl. No.: 09/740,765

(22) Filed: Dec. 19, 2000

(51) Int. Cl.$^7$ ............................................. A61C 3/02
(52) U.S. Cl. ................................................... 433/142
(58) Field of Search ............................ 433/141, 142, 433/143, 144, 125, 146

(56) References Cited

U.S. PATENT DOCUMENTS

| | | | |
|---|---|---|---|
| 491,464 A | | 2/1893 | Blake, Sr. |
| 614,723 A | * | 11/1898 | Jackson ............... 433/142 |
| 815,153 A | | 3/1906 | Fritz |
| 1,050,469 A | * | 1/1913 | Keifer ............... 433/142 |
| 1,201,875 A | * | 10/1916 | Russ ............... 433/142 |
| 1,707,952 A | | 4/1929 | Schneider |
| 2,029,495 A | | 2/1936 | Lowe ............... 128/305 |
| 2,655,726 A | | 10/1953 | Diener ............... 32/46 |
| 3,325,900 A | | 6/1967 | Sohlberg ............... 32/46 |
| 4,319,876 A | | 3/1982 | Murnoka ............... 433/141 |
| D265,004 S | | 6/1982 | Davis ............... D28/64 |
| 4,365,957 A | | 12/1982 | Das ............... 433/144 |
| 4,592,729 A | * | 6/1986 | Bilciurescu ............... 433/142 |
| 4,820,154 A | | 4/1989 | Römhild et al. ............... 433/128 |
| 4,836,781 A | | 6/1989 | Meinershagen ............... 433/141 |
| 4,854,867 A | | 8/1989 | Meinershagen ............... 433/40 |
| 4,952,213 A | | 8/1990 | Bowman et al. ............... 606/79 |
| D311,595 S | | 10/1990 | Ewald ............... D28/64 |
| 5,084,978 A | | 2/1992 | McReynolds ............... 30/517 |
| 5,118,291 A | | 6/1992 | Varaine ............... 433/142 |
| 5,682,665 A | | 11/1997 | Svanberg ............... 29/458 |

* cited by examiner

*Primary Examiner*—Nicholas D. Lucchesi
(74) *Attorney, Agent, or Firm*—Moore & Van Allen PLLC; Michael G. Johnston

(57) ABSTRACT

A dental tool is provided for use in removing solidified material from on and between teeth during restorations. The new dental tool is appropriately shaped to provide proper control and visualization of the work and prevent damage to the interior of the mouth. The dental tool comprises a handle portion and a blade support portion extending from the handle portion, wherein the longitudinal axis of the handle and blade support portions form an angle of from about 130 degrees to about 140 degrees. A blade member is supported on the distal end of the blade support portion including a support surface which is in a plane which forms an angle of from about 80 degrees to about 100 degrees with the longitudinal axis of the handle portion. The blade supporting portion comprises a pair of spaced arms projecting from the handle and at an angle relative to one another in the range of from about 10 to about 25 degrees. The distal end portion of the spaced arms terminate in bosses, preferably barbs for supporting the blade member. The blade member has mounting holes on each end for receiving the bosses on the ends of the arms. The blade member is fixed to the ends of the arms by compressing the arms inwardly to accommodate the mounting holes in the blade member. Thus, the blade member is quickly and easily replaceable.

20 Claims, 2 Drawing Sheets